United States Patent [19]
Dufresne et al.

[11] Patent Number: 4,917,093
[45] Date of Patent: Apr. 17, 1990

[54] BIOLOGICAL TISSUE STIMULATOR WITH ADJUSTABLE HIGH VOLTAGE POWER SUPPLY DEPENDENT UPON LOAD IMPEDANCE

[75] Inventors: Joel R. Dufresne, St. Paul; William L. Sondermann, Minneapolis, both of Minn.

[73] Assignee: Minnesota Mining and Manufacturing Company, St. Paul, Minn.

[21] Appl. No.: 61,695

[22] Filed: Jun. 12, 1987

[51] Int. Cl.⁴ .............................................. A61N 1/00
[52] U.S. Cl. ................................... 128/421; 128/422; 128/734
[58] Field of Search ................... 128/421, 422, 419 R, 128/783, 784, 734, 419 D, 419 PG

[56] References Cited
U.S. PATENT DOCUMENTS

| | | | |
|---|---|---|---|
| 4,595,010 | 6/1986 | Radke | 128/421 |
| 4,630,615 | 12/1986 | Yomtov | 128/734 |
| 4,665,920 | 5/1987 | Campbell | 128/421 |
| 4,694,830 | 9/1987 | Lekholm | 128/419 PG |
| 4,706,674 | 11/1987 | Dieken et al. | 128/419 R |
| 4,771,781 | 9/1988 | Lerman | 128/419 D |
| 4,790,318 | 12/1988 | Elmqvist et al. | 128/419 PG |

Primary Examiner—Francis Jaworski
Assistant Examiner—George Manuel
Attorney, Agent, or Firm—Donald M. Sell; Walter N. Kirn; William D. Bauer

[57] ABSTRACT

A biological tissue stimulator is disclosed having an adjustable high voltage power supply. The high voltage power supply is coupled to a battery producing a high voltage signal to be supplied to an output circuit for supplying an electrical stimulation signal of a predetermined current amplitude. An electrode is coupled to the electrical stimulation pulse and is adapted to be coupled to the biological tissue to deliver the electrical stimulation signal to the biological tissue. An adjustment mechanism is coupled to the output stage and to the adjustable high voltage power supply for comparing the amplitude of the high voltage signal to the amplitude of the voltage drop across the biological load and adjusting the amplitude of the high voltage signal dependent upon the result of that comparison. The adjustment mechanism adjusts the amplitude of the high voltage signal to minimize the difference in the amplitude between the high voltage signal and the voltage drop across the biological load thereby maximizing the energy efficiency of the biological tissue stimulator.

11 Claims, 6 Drawing Sheets

BIOLOGICAL TISSUE STIMULATOR WITH ADJUSTABLE HIGH VOLTAGE POWER SUPPLY DEPENDENT UPON LOAD IMPEDANCE

BACKGROUND OF THE INVENTION

The present invention relates generally to biological tissue stimulators and more particularly to biological tissue stimulators utilizing a constant current output stage.

Biological tissue stimulators are known to be medically useful. In one example, a transcutaneous electrical nerve stimulator (TENS) is utilized to mask pain signals in a human body before they reach the brain, giving the subject apparent relief from the pain. In such a TENS device, electrical stimulation pulses, usually current pulses of a selected rate, amplitude, pulse width and duty cycle, are delivered to the skin of the subject by one or more electrodes, each containing a pair of electrode elements. The timing characteristics of the delivered electrical stimulation pulses may be predetermined, as for example, by the prescribing physician and/or may be individually selected or controlled by switches available to be operated by the subject. Additionally, individual parameters, or even entire pulse programs, can be varied in a predetermined or random basis by the TENS device itself.

Another example of a useful biological tissue stimulator is a neuromuscular stimulator (NMS) which can be utilized to electrically stimulate muscle activity of a patient. Electrical stimulation pulses, again probably current pulses of a carefully controlled rate, amplitude, pulse width and sequence are delivered by one or more pairs of electrodes to a site or sites near the muscle to be stimulated in order to activate or contract the muscle. The initiation and control of such sequence of pulses may be patient-controlled.

Biological tissue stimulators typically provide a series of electrical stimulation pulses to the biological tissue according to a preset program. It is generally desirable to provide an electrical stimulation pulse of a known current value. Output circuits are commonly arranged to produce so-called "constant current" outputs. The output stage of a biological tissue stimulator sees a load impedance which consists primarily of the electrode-tissue interface impedance and the impedance of the biological tissue between the electrode elements. This impedance can vary significantly, for example, from about 200 ohms to 2500 ohms. The "constant current" output stage supplies the same current to the worst-case expected load impedance, i.e., the highest expected load impedance, as to a more normal (lower) load impedance. The high voltage power supply driving the output stage must be able to deliver a high enough voltage to maintain the desired current level through this "worst-case" load impedance. If the high voltage power supply output level is fixed at this maximum value, however, then a much higher voltage is supplied to the output stage than is otherwise required when the load impedance is in a lower, more normally anticipated, range. This excess high voltage power is then dissipated and "lost", resulting in an energy-inefficient use of such a high voltage supply.

It is highly desirable that biological tissue stimulators be portable devices, that is, be compact in size and low in weight Both attributes make for a more comfortable and easily used biological tissue stimulator. The biological tissue stimulator may be required to be connected to the body for extended periods of time and, thus, ease of portability and unobtrusivness are of critical importance.

For portability, biological tissue stimulators must be battery-powered since connection to a household power supply would greatly limit the geographical range of operation. It is advantageous that the battery life of the biological tissue stimulator be as long as possible. Insufficient battery life limits the freedom of extensive use without resupply, creates the bothersome duty of physically changing the batteries and substantially increases the cost of operation. Also, the deterioration of battery voltage may result in less than optimum performance characteristics. If the battery discharges more often, a greater percentage of time may be spent during nonoptimum operating conditions and, thus, the biological tissue stimulator may not achieve the advantageous results that it was intended to produce.

Battery life may be increased by increasing the size and weight of the batteries. This, however, is not desirable since increasing of the size and weight of the biological tissue stimulator limits the places, locations and environments for the biological tissue stimulator is likely to be used. Thus, a heavy, bulky biological stimulator is not truly portable.

SUMMARY OF THE INVENTION

The present invention provides a biological tissue stimulator with a substantially improved battery life over a similar stimulator without the high voltage adjustment feature of the present invention.

Since the actual load impedance is not known and may vary over the course of time, the biological tissue stimulator of the present invention implicitly determines that impedance by comparing the output signal of the high voltage power supply against the voltage actually dissipated across the load impedance. This is accomplished by measuring the "left over" voltage from the high voltage power supply at the end of an electrical stimulation pulse. If sufficient excess voltage is available, the output voltage of the adjustable high voltage power supply can be decreased. Thus, the next electrical stimulation pulse will be associated with a lower amount of excess high voltage. This process is then repeated over successive electrical stimulation pulses. Through this iterative process, eventually a level of high voltage is reached which does not significantly waste high voltage power.

Since each step of this iterative process typically occurs in a time of much less than a second, the biological tissue stimulator will quickly, compared to the lifetime of the batteries, reach the desired high voltage level. Since the load impedance is usually known to change only gradually, the iterative process typically will reach a relative steady state without significant load impedance changes. If the required current amplitude output should change, as e.g., by a manual change in the amplitude controlled by the patient or automatically under stimulation program control, the high voltage signal again will seek the minimum required level to maintain constant current.

Should the amount of high voltage signal available ever be insufficient to supply the required current output of the electrical stimulation pulse, then the high voltage power supply adjusts the high voltage signal by increasing its output voltage level until the required current level or amplitude is reached. Again, this can be done iteratively over a successive number of electrical stimulation pulses. Alternatively, instead of iteratively increasing the high voltage stepwise by known or relatively small calculated steps, it may be wise to immediately step the high voltage to the maximum possible level. This would ensure that as much of the required electrical stimulation program is run as is possible. Current would not be lost while the high voltage power supply incrementally attained the higher required level. Since the measurement of the insufficient high voltage signal occurs with an actual load, the high voltage signal will be insufficient until it can be properly readjusted over at least one electrical stimulation pulse. After the high voltage signal is deemed insufficient and raised to its maximum level, the automatic decreasing steps previously described can occur again ensuring that no major amount of battery life is lost.

Thus, the biological tissue stimulator of the present invention is adapted to supply an electrical stimulation signal to a biological load. The stimulator has a battery and a high voltage power supply operatively coupled to the battery producing a high voltage signal. An output circuit is coupled to the high voltage signal for supplying the electrical stimulation signal of a predetermined current amplitude. Electrodes are coupled to the electrical stimulation pulse and adapted to be coupled to biological tissue and deliver the electrical stimulation signal so that the electrical stimulation signal may be applied to the biological tissue. An adjustment circuit is coupled to the output circuit and to the high voltage power supply for comparing the amplitude of the high voltage signal to the amplitude of the voltage drop across the biological load and then adjusting the amplitude of the high voltage signal dependent upon the result of the comparing. It is preferred that the adjustment circuit adjust the amplitude of the high voltage signal to minimize the difference in amplitude between the high voltage signal and the voltage drop across the biological load thereby maximizing the energy efficiency of the biological stimulator. Further, it is preferred that the high voltage power supply be a switching type power supply with the amplitude of the high voltage signal being dependent upon control signals generated by an adjustment circuit.

It is preferred that the adjustment circuit include a voltage gating circuit coupled to the output circuit for gating a slack voltage representing the voltage from the high voltage signal not dissipated across the biological load. A comparison circuit coupled to the slack voltage then compares the slack voltage against a predetermined reference voltage producing a comparison output indicative of such comparison relative to a predetermined threshold. The adjustment circuit then further has a switching circuit coupled to the comparison circuit and to the high voltage power supply for supplying control signals so that the amplitude of the high voltage signal is properly adjusted relative to the predetermined threshold. In another embodiment, the slack voltage is compared against first and second predetermined reference voltages providing a "window" between which the slack voltage would be allowed to range.

In one embodiment of the present invention, the adjustment circuit of the biological tissue stimulator determines the impedance of the biological load and adjusts the amplitude of a high voltage signal to minimize the amplitude of the high voltage signal and still have sufficient voltage amplitude to allow the output circuit to produce the electrical stimulation signal at a predetermined current amplitude.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
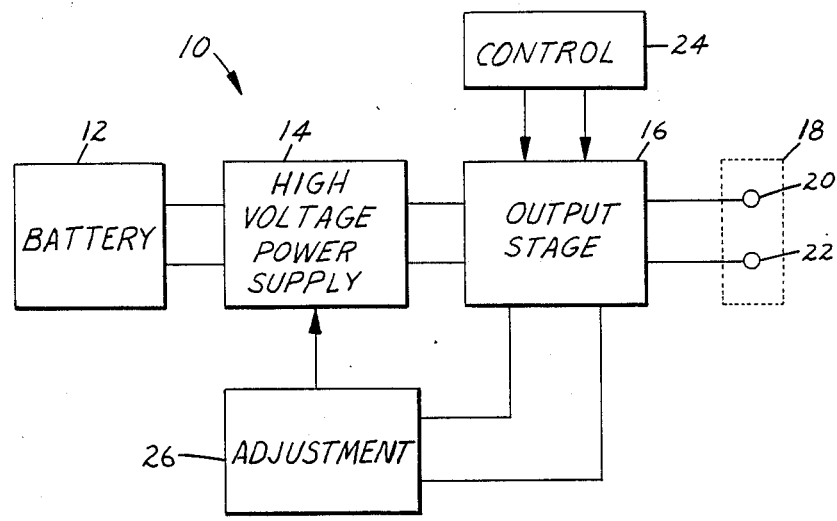
FIG. 1 is block diagram of one embodiment of the present invention.

A block diagram of the biological tissue stimulator 10 of the present invention is illustrated in FIG. 1. A battery 12, of conventional design, provides a portable compact energy source for the biological tissue stimulator 10. The low voltage power provided by the battery 12 is supplied to a high voltage power supply 14. High voltage power supply 14 steps up the low voltage supply of the battery 12 to a high voltage signal which is delivered to the output stage 16. Output stage 16 supplies an electrical stimulation pulse to an electrode system 18, consisting of electrode elements 20 and 22. Electrode system 18 is designed to be attached to biological tissue so that the output stage 16 can deliver an electrical stimulation pulse to electrode elements 20 and 22 by passing a current of known value between electrode elements 20 and 22, thereby stimulating the biological tissue Since it is generally the current through the biological tissue which determines the therapeutic advantage obtained by the biological tissue stimulator, output stage 16 delivers an electrical stimulation pulse which is of a known and predetermined current amplitude. The particular electrical stimulation pulse to be delivered is determined by control section 24. Control section 24 determines the particular electrical stimulation pulse to be delivered, either directly from the amplitude control operated by the user of the biological tissue stimulator, from a fixed set of operating parameters (e.g., pulse rate, width and amplitude) stored in the biological tissue stimulator 10, or as selected from one of a number of preprogrammed stimulation programs which may vary the operating parameters of the electrical stimulation pulses. Control section 24 is of conventional design and is well known in the art. Similarly, electrode system 18 is of conventional design and well known with respect to biological tissue stimulators 10.

The load for the output stage 16 is determined primarily from the electrode-biological tissue interface impedance, which is essentially the impedance at the point of contact between electrode elements 20 and 22 with the biological tissue, and the impedance of the biological tissue between electrode elements 20 and 22. When electrode system 18 is coupled to the biological tissue (not shown), the output stage 16 will adjust the voltage of the electrical stimulation pulse to ensure that the proper predetermined current amplitude of the electrical stimulation pulse is maintained, as determined by control section 24. To be able to supply the proper current amplitude for the electrical stimulation pulse delivered to electrode system 18, output stage 16 must have a sufficient operating voltage from high voltage power supply 14 to enable output stage 16 to deliver the proper current amplitude under worst-case load impedance conditions. In these worst-case load impedance conditions, the combined impedance of the electrode system 18's biological tissue interface, the electrode systems and the biological tissue impedance is high, requiring a large voltage to supply the proper electrical stimulation pulse of proper current amplitude. However, when the output load impedance levels are at more "normal" levels, a lower high voltage signal is required by output stage 16 and, hence, required from high voltage power supply 14. If the worst-case high voltage signal level is maintained, then a substantial amount of power and, hence, energy from battery 12 is lost or dissipated in the circuitry not across the biological tissue when the load impedance is not at its maximum value. Hence, the biological tissue stimulator 10 of the present invention has an adjustment circuit 26 coupled to the output stage 16. The adjustment circuit 26 compares the amplitude of the high voltage signal delivered to the output stage 16 by the high voltage power supply 14 with the actual voltage drop across the load impedance and, hence, can determine whether there is excess high voltage signal available and, hence, whether energy from the battery 12 is being wasted. Adjustment circuit 26 then supplies control signals to high voltage power supply 14 in order to adjust the amplitude of the high voltage signal which high voltage power supply 14 delivers to the output stage 16. Usually this is done to minimize the difference between the voltage supplied by the high voltage power supply to the output stage 16 and the actual voltage drop across the load impedance. Alternatively, adjustment circuit 26 may determine the actual impedance of the biological load, or load impedance, directly and then send control signals to the high voltage power supply 14 to minimize the high voltage signals supplied by the high voltage power supply 14 to minimize the high voltage signal supplied by the high voltage power supply 14 to the output stage 16 and still allow the output stage 16 to produce the electrical stimulation pulse of the proper current amplitude.

Figure 2:
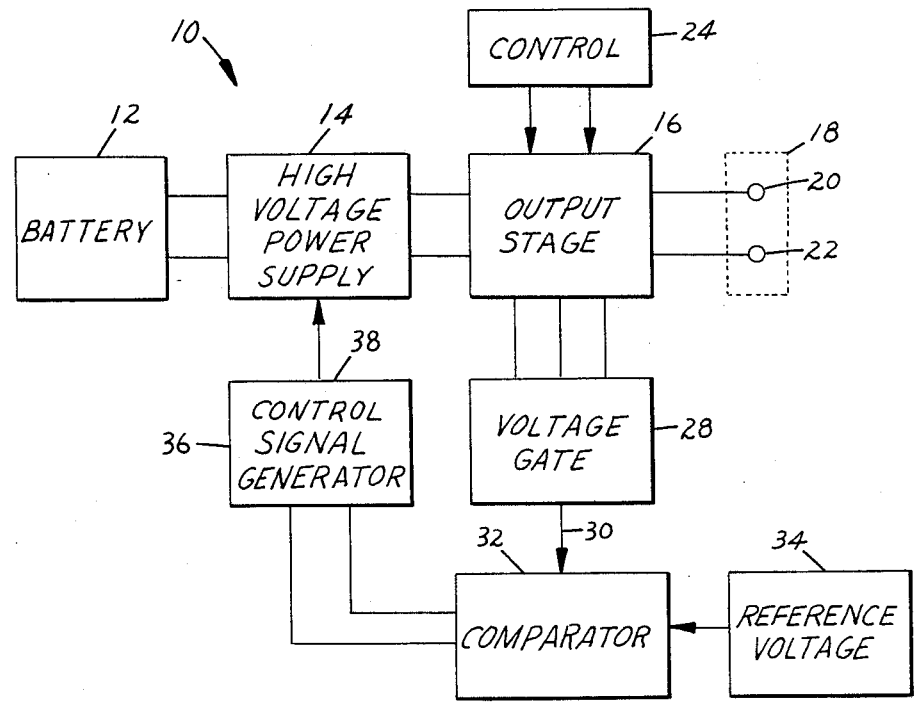
FIG. 2 is a block diagram of an alternative embodiment of the present invention.

More detail of the adjustment circuit 26 can be seen in the biological tissue stimulator 10 illustrated in FIG. 2. The biological tissue stimulator 10 again has battery 12, the same adjustable high voltage power supply 14, the same output stage 16, the same electrode system 18 and the same control section 24. Voltage gating circuit 28 is coupled directly to output stage 16 which gates a "slack" voltage 30 representing the amount of the output voltage from the adjustable high voltage power supply 14 delivered to the output stage 16 which is not dissipated across the biological load impedance through electrode system 18. This amount of slack voltage 30 represents the excess in amplitude of the high voltage signal delivered by the high voltage power supply 14 to the output stage 16 over and above what is required to maintain the proper current amplitude of the electrical stimulation pulse supplied by output stage 16 to electrode system 18. A comparator 32 then compares slack voltage 30 against a known reference voltage 34 and sends a comparison output indicative of the result of such comparison to control signal generator 36. Reference voltage 34 is selected to be larger than zero in order to minimize the amount of hunting that otherwise would result in constant readjustment of the high voltage signal amplitude level but yet sufficiently small so as to substantially minimize the waste of the energy of battery 12. Generally, with a high voltage signal which varies in the range of 10 to 75 volts, a reference voltage of 6 volts is tolerable. In this embodiment, high voltage power supply 14 is a switching type power supply. That is, high voltage power supply 14 operates to step up the low voltage level of battery 12 to the high voltage signal level through a series of intermittent connections of the battery 12 to an inductor, successively "stepping up" the voltage level across the inductor. The successive connections of battery 12 to the inductor in the high voltage power supply 14 is controlled by control signals 38 supplied from the control signal generator 36. Thus, the control signal generator, through the application of control signals 38, can directly vary the amplitude of the high voltage signal delivered from the high voltage power supply 14 to the output stage 16. Should the result of the comparison made by comparator 32 with the reference of voltage 34 indicate that there is an excess of slack voltage 30, then control signal generator 36 will vary the application of control signals 38 to the high voltage power supply 14 so as to lower the amplitude of the high voltage signal delivered from the high voltage power supply 14 to the output stage 16. Should the result of comparator 32 in comparing a slack voltage 30 to the reference voltage 34 indicate that the slack voltage 30 is insufficiently high, then an increased output level from high voltage power supply 14 is called for. Thus, the control signal generator 36 would modify the control signals 38 sent to the high voltage power supply 14 to increase the amplitude of the high voltage signal delivered from the high voltage power supply 14 to the output stage 16.

Figure 3:
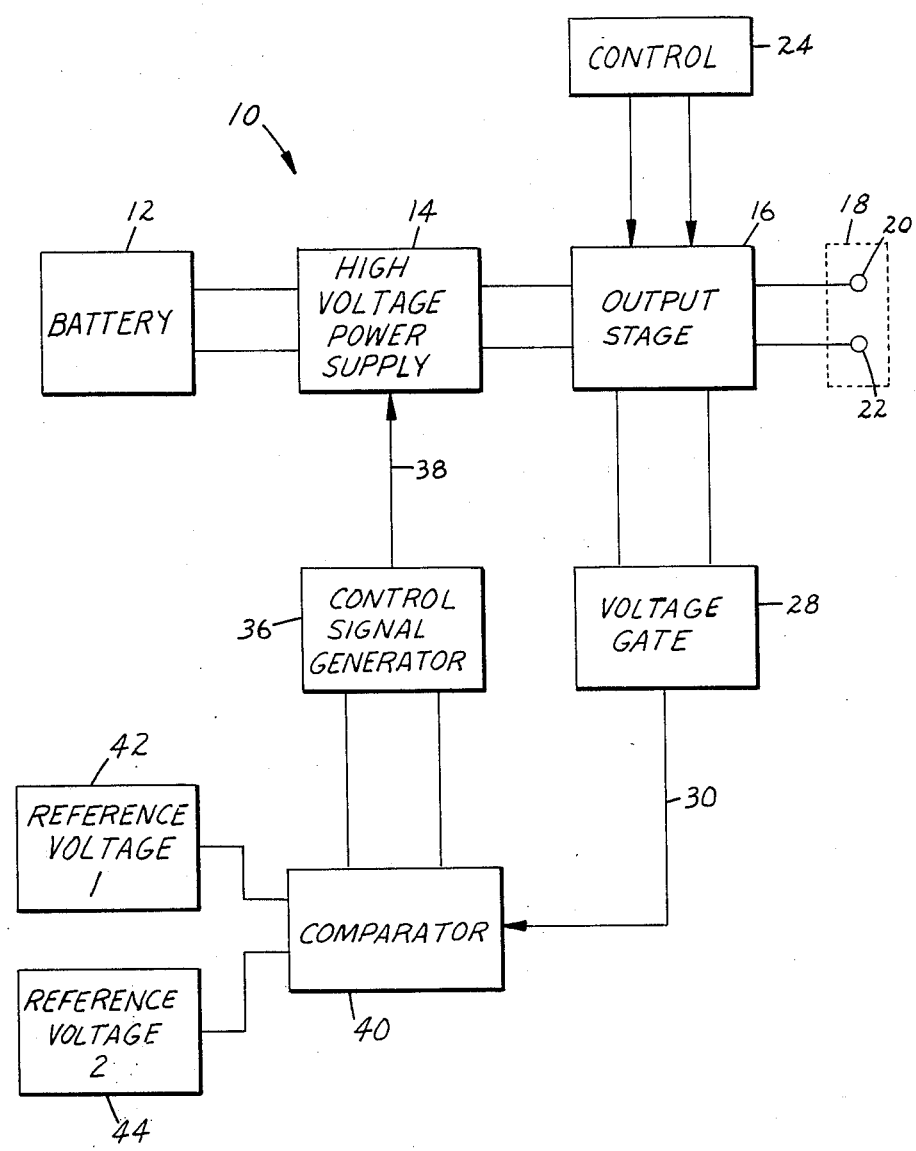
FIG. 3 is a block diagram of another alternative embodiment of the present invention.

FIG. 3 illustrates a block diagram for an alternative embodiment of the biological stimulator 10 of the present invention. Battery 12, high voltage power supply 14, output stage 16, electrode 18, control section 24, voltage gate 28 are identical to corresponding elements described in FIG. 2. In this embodiment, however, a comparator 40 compares slack voltage 30 against a first reference voltage 42 and against a second reference voltage 44. The value of the second reference voltage 44 is chosen to be greater than the value of the first reference voltage 42 so as to create a "window" or range between which slack voltage 30 is allowed to fluctuate without resulting in changes in the control signals 38 delivered by control signal generator 36. Should comparator 40 indicate that slack voltage 30 exceeds the second reference voltage 44 then control signal generator 36 will modify the control signals 38 to decrease the amplitude of the high voltage signal delivered from the high voltage power supply 14 to the output stage 16 since the excess amount of slack voltage 30 indicates that energy from the battery 12 is being wasted. Should, however, comparator 40 indicate that slack voltage 30 is less than the first reference voltage 42, then the level of high voltage signal from high voltage power supply 14 to output stage 16 is nearly or is insufficient. Thus, control signal generator 36 will modify control signals 38 to the high voltage power supply 14 in order to increase the amplitude of the high voltage signal delivered to the output stage 16.

Figure 4:
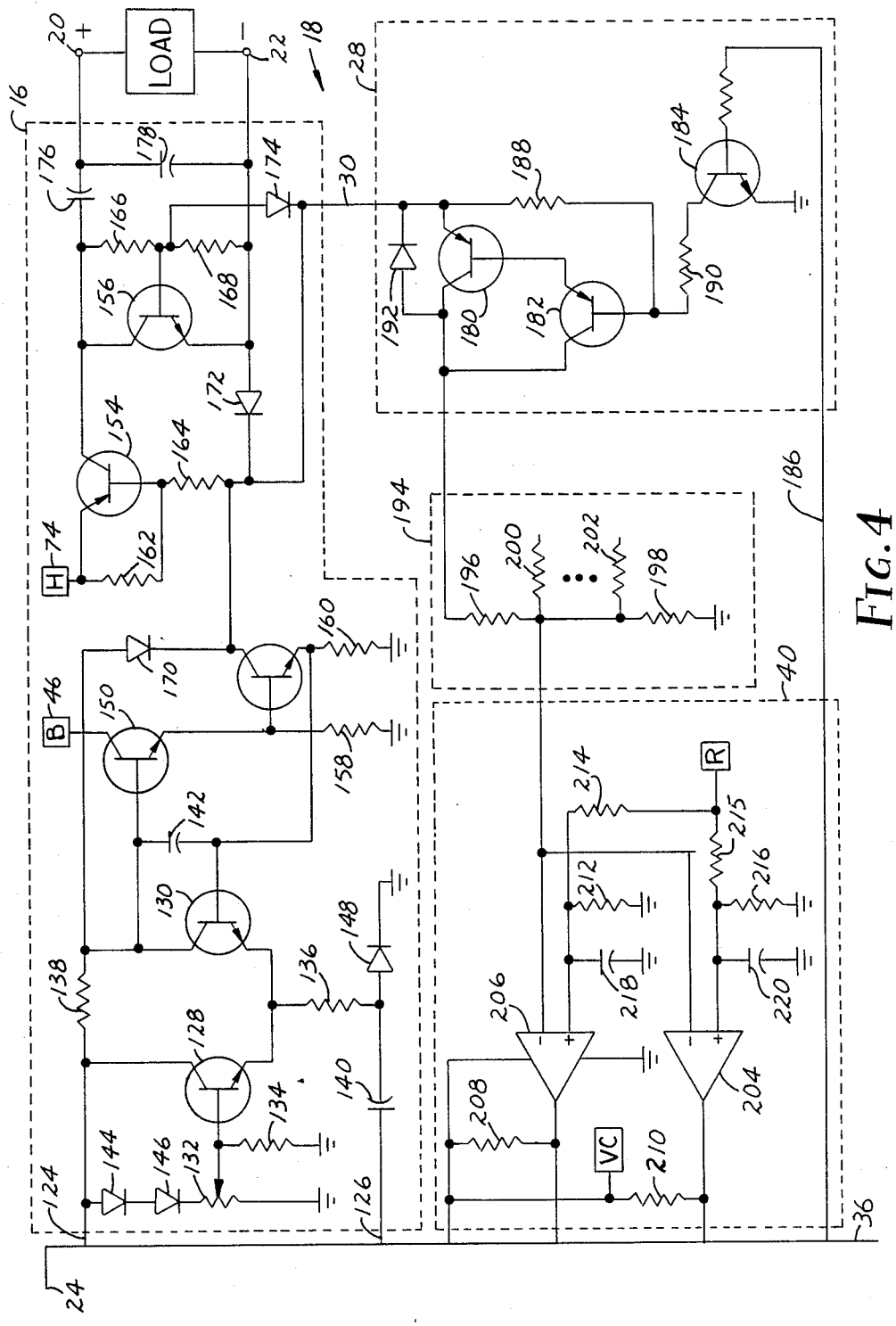
FIG. 4 is a schematic diagram of a portion of one embodiment of the present invention.
Figure 5:
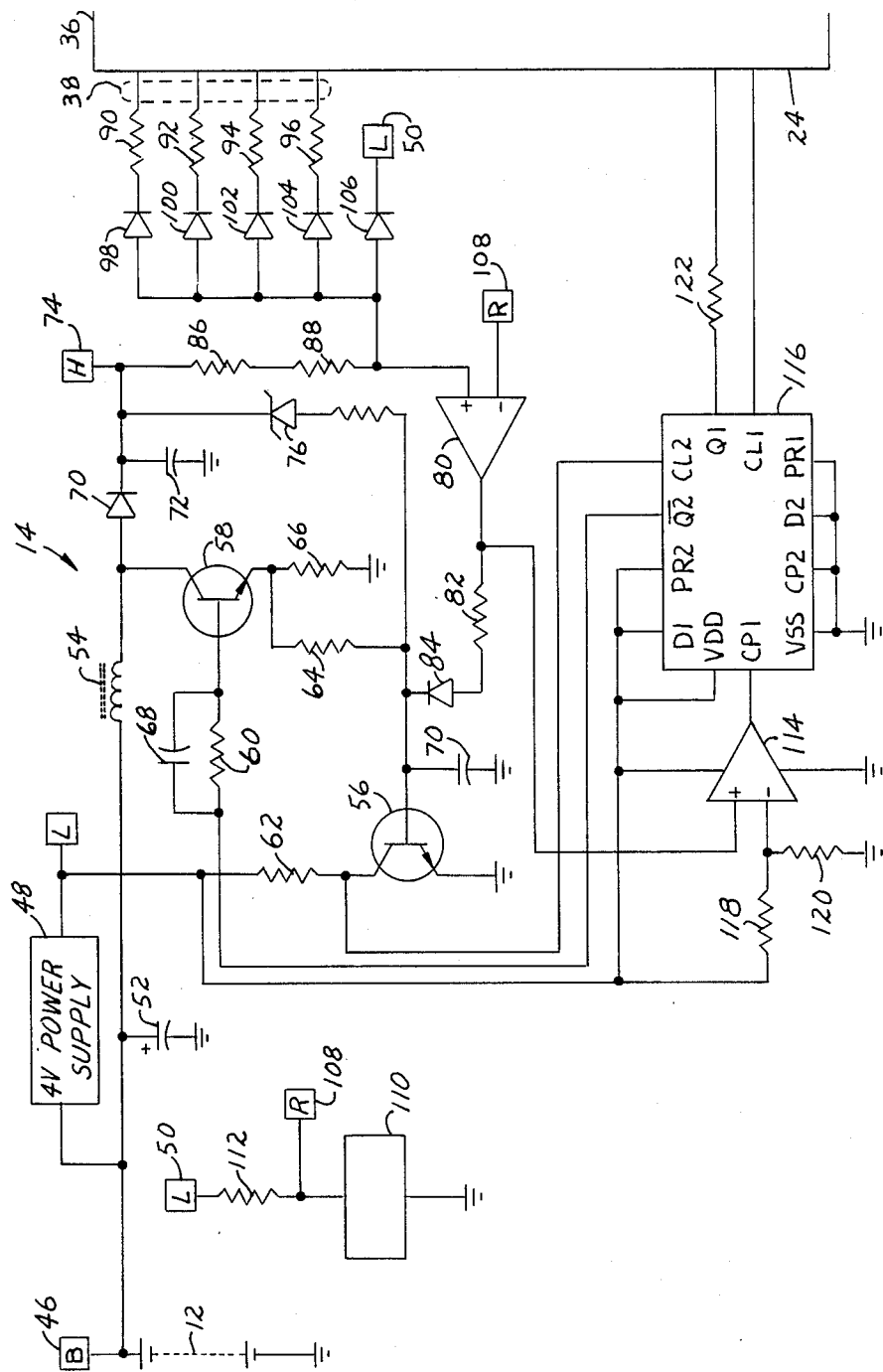
FIG. 5 is a schematic diagram of another portion of one embodiment of the present invention.

A detailed schematic diagram of the biological tissue stimulator 10 of the present invention is illustrated in FIGS. 4 and 5. Battery 12 is shown supplying a battery voltage 46 and is shown connected to a conventional four volt power supply 48 for supplying conventional logic voltage 50 to run the integrated circuits in the accompanying schematic. Battery 12 is a nine volt (nominal) battery. Battery voltage 46 is connected through a filter capacitor 52 to an inductor 54 as part of the high voltage power supply 14. This circuit uses a power oscillator circuit incorporating transistors 56 and 58 as well as accompanying components resistors 60, 62, 64, 66 and capacitors 68 and 70. This power oscillator circuit generators transients across inductor 54 which are rectified by diode 71 and filtered by capacitor 72 to achieve a positive direct current output voltage which is the high voltage signal 74 delivered by the high voltage power supply 14 to the output stage 16. Zener diode 76 and accompanying resistor 78 provide a safety mechanism preventing the high voltage signal 74 from exceeding a known preset value. The power oscillator circuit of the high voltage power supply 14 is gated by comparator 80 through resistor 82 and diode 84 according to the voltage monitored from the programmable divider circuit of resistors 86, 88, 90, 92, 94 and 96 and associated diodes 98, 100, 102, 104 and 106. The other side of the input to comparator 80 is obtained from reference voltage 108 which is obtained via voltage reference signal circuit 110 and associated resistor 112 coupled to the logic power supply 50 providing a known stable reference voltage 108. Comparator 114 and dual flip-flop 116 along with associated resistors 118, 120 and 122 permit disabling of the high voltage power supply from control circuit 24.

Control circuit 24 also supplies a true level enable signal 124 and its complement 126 to output stage 16. This supplies both positive and negative power for the differential amplifier circuit consisting of transistors 128 and 130, associated resistors 132, 134, 136, 138, capacitors 140, 142, and diodes 144, 146 and 148. The current level provided by this output stage 16 is determined by the wiper at variable resistor 132, as for example, being an amplitude control potiometer controlled by the user. The remainder of the current controlled output stage 16 is formed from transistors 150, 152, 154, 156, resistors 158, 160, 162, 164, 166, 168, diodes 170, 172, 174 and capacitors 176 and 178. Transistor 154 is driven from the high voltage signal 74 as obtained from the high voltage power supply 14. The signal across capacitor 178 is supplied to electrode system 18 for delivery to the biological tissue load.

Slack voltage 30 is obtained from the collector of transistor 152 and routed to the voltage gate circuit 28. Here it is applied to series pass transistor 180. Transistors 182 and 184 provide base drive to transistor 180 whenever the enable signal 186 is obtained from control circuit 24. Resistors 188, 190 and diode 192 complete the voltage gating circuit. Voltage gating circuit 28 operates to supply the slack voltage 30 which exists at the end of the electrical stimulation pulse which most closely approximates the excess voltage available from high voltage signal 74. In this embodiment, the output from voltage gating circuit 28 supplied optionally to voltage attenuation circuit 194 which through resistors 196 and 198 serve to reduce the voltage to the proper level for subsequent processing. Also, resistors 200 and 202 serve to represent other possible inputs from other channels of the biological tissue stimulator to show that a single comparator 40 can serve a plurality of output stages 16 representing different channels of output of the biological tissue stimulator 10. The output of voltage attenuation 194 is supplied to comparator 40. Comparator 204 provides a low comparison threshold of four volts and comparator 206 provides a high comparison threshold of ten volts for the window comparator as described in the block diagram of FIG. 3. The lower threshold voltage of four volts is chosen to permit electrical stimulation pulses having a current amplitude of 80 milliamperes through large load impedances and resistor 160 and transistor 152. The upper voltage threshold of ten volts was chosen to accomodate the "quantal" magnitude of adjustments for the high voltage power supply 14 provided by the programmable voltage divider of FIG. 5. Resistors 208, 210, 212, 214, 216 and capacitors 218 and 220 complete the comparator circuit 40 is supplied to control circuit 24, a portion of which serves as the control signal generator 36 of the block diagram of FIG. 3. This portion of control section 24, representing the control signal generator 36, supplies the control signals across the programmable voltage divider of FIG. 5 to supply the control signals to the power oscillator circuit of the high voltage power supply of FIG. 5.

The component values illustrated in the schematic diagram of FIGS. 4 and 5 are shown in the following table:

| Reference Numeral | Value or Component Number |
| --- | --- |
| 52 | 6.8 microfarads, 16 volts |
| 54 | 1.1 millihenries |
| 56 | BC848C |
| 58 | BST52 |
| 60 | 2.2 kilohms |
| 62 | 100 kilohms |
| 64 | 100 kilohms |
| 66 | 3.3 kilohms |
| 68 | 0.01 microfarads |
| 70 | 33 picofarads |
| 71 | BAS19 |
| 72 | 6.8 microfarads, 80 volts |
| 76 | BZX84-C75 |
| 78 | 510 kilohms |
| 80 | IR-9022N |
| 82 | 100 kilohms |
| 84 | BAV 70 |
| 86 | 8.2 megohms |
| 88 | 1 megohm |
| 90 | 249 kilohms |
| 92 | 499 kilohms |
| 94 | 1 megohm |
| 96 | 2 megohms |
| 98 | BAW56 |
| 100 | BAW56 |
| 102 | BAW56 |
| 104 | BAW56 |
| 106 | BAW56 |
| 110 | LM385BZ-1.2 |
| 114 | IC-5B |
| 116 | HEF4013BT |
| 118 | 1 megohm |
| 120 | 1 megohm |
| 122 | 100 kilohms |
| 128 | BC848C |
| 130 | BC848C |
| 132 | 47 kilohms, adjustable |
| 134 | 47 kilohms |
| 136 | 13.7 kilohms |
| 138 | 15 kilohms |
| 140 | 1 microfarad |
| 142 | 100 picofarads |
| 144 | BAV99 |
| 146 | BAV99 |

| Reference Numeral | Value or Component Number |
| --- | --- |
| 148 | BAV70 |
| 150 | BC846B |
| 152 | BSR43 |
| 154 | MMBT5401 |
| 156 | BSR43 |
| 158 | 1 kilohm |
| 160 | 26.7 ohms |
| 162 | 12 kilohms |
| 164 | 33 kilohms |
| 166 | 100 kilohms |
| 168 | 100 kilohms |
| 170 | BAV70 |
| 172 | BAV70 |
| 174 | BAV70 |
| 176 | 6.8 microfarads, 50 volts |
| 178 | 470 picofarads |
| 180 | MMBT5401 |
| 182 | MMBT5401 |
| 184 | BC846B |
| 188 | 5.6 megohms |
| 190 | 5.6 megohms |
| 192 | BAV70 |
| 196 | 1 megohm |
| 198 | 100 kilohms |
| 200 | 1 megohm |
| 202 | 1 megohm |
| 204 | LM239D |
| 206 | LM239D |
| 208 | 10 kilohms |
| 210 | 10 kilohms |
| 212 | 1 megohm |
| 214 | 100 kilohms |
| 215 | 1 megohm |
| 216 | 499 kilohms |
| 218 | 0.047 microfarads |
| 220 | 0.047 microfarads |

Figure 6:
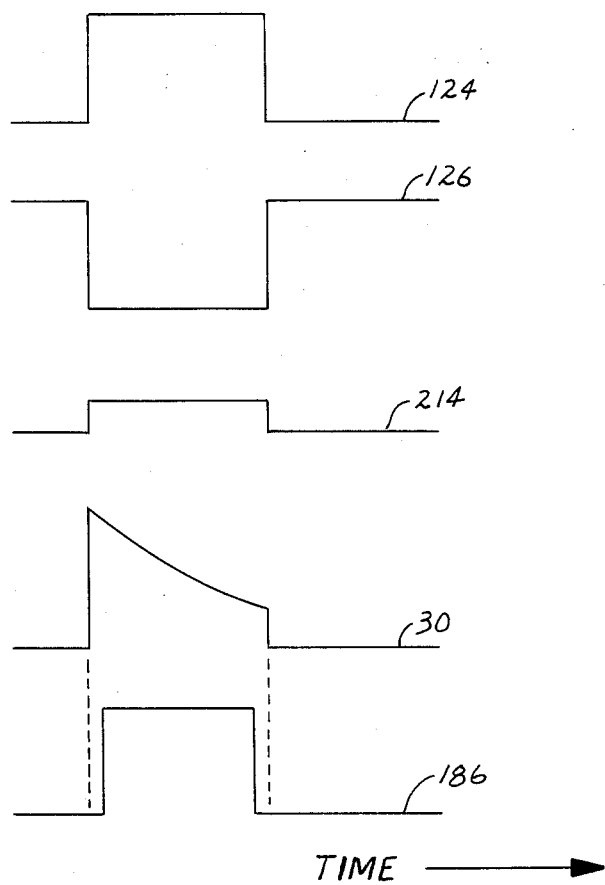
FIG. 6 is a timing diagram of electrical signals of the present invention.

The timing diagram of FIG. 6 shows the output circuit 16 enable signals 124 and its complement 126 representing the enabling of this particular output stage 16 and the accompanying output electrical stimulation pulse 214 delivered to electrode system 18. The slack voltage signal 30 shows the high voltage signal 74 being dissipated across a highly capacitive biological load, through the electrode system 18, from a maximum value near the start of the output stage enable and exponentially decreasing as the power from the high voltage signal 74 is dissipated across the biological load. As can be seen in the exemplary timing diagram of FIG. 6, not all of the high voltage signal 74 is dissipated across the biological load. Thus, at the end of the output stage enable a discrete amount of slack voltage 30 remains. From this is can be seen that slack voltage 30 must be measured only at the end of the output stage enable signal. Since only at this time does the slack voltage 30 represent the excess in high voltage signal not dissipated across the biological load.

Figure 7:
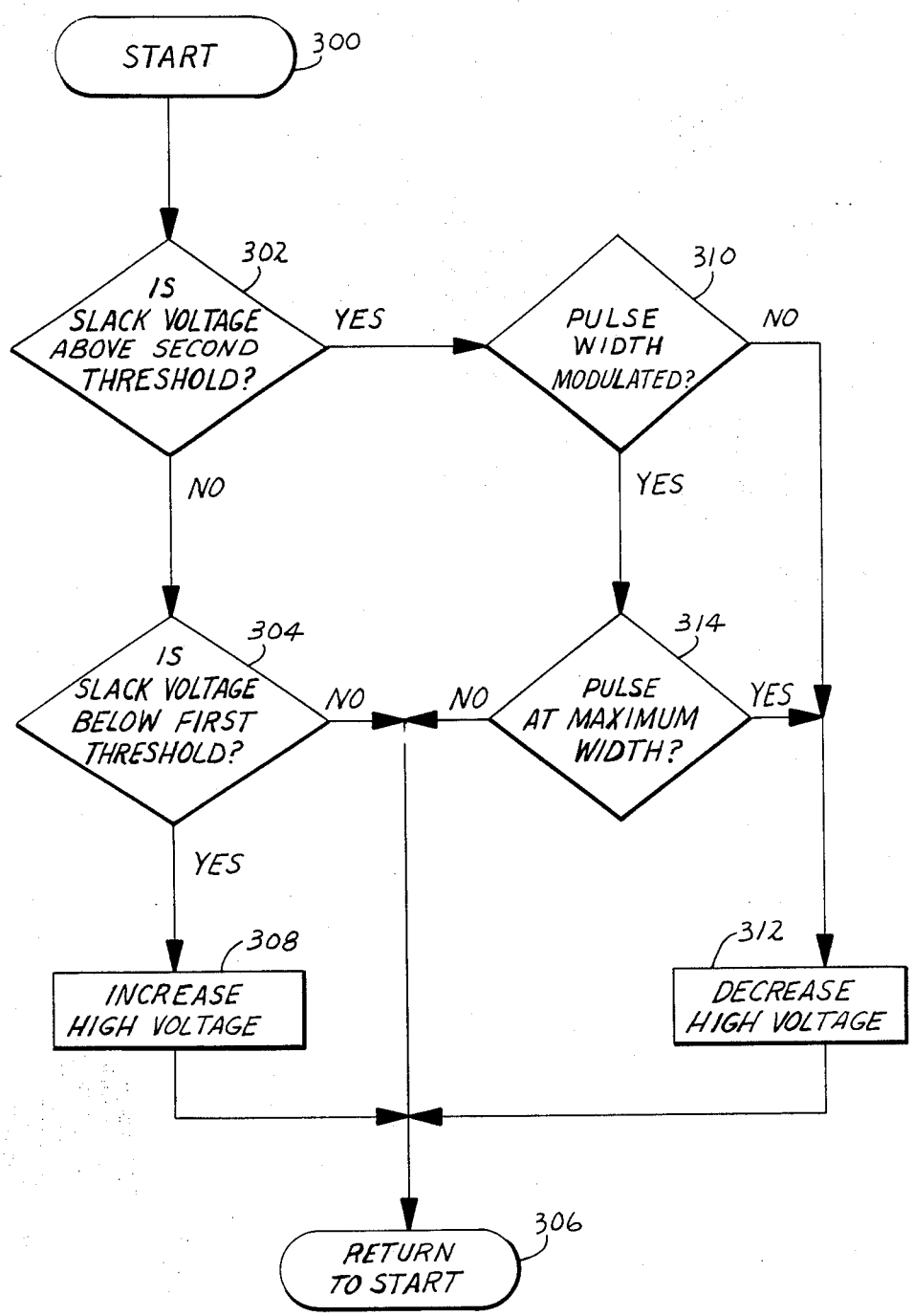
FIG. 7 is flow chart of increase/decrease decisions of the control portion of the present invention.

The flow chart of FIG. 7 may be utilized by the control signal generator 36 to determine when to modify the control signals 38 to increase the high voltage signal 74 or when to modify the control signals 38 in order to decrease the high voltage signal 74. As can be seen in the flow chart, the process is started in block 300. The control signal generator at block 302 first determines whether the slack voltage 30 as measured by comparator 40 is above the second reference voltage threshold. If the slack voltage is not above the second reference voltage threshold, the flow chart at block 304 determines whether the slack voltage 30 is below the first reference voltage threshold. If the slack voltage 30 is not below the first reference voltage threshold, this indicates that slack voltage 30 is within the window of allowable slack voltages and the control signal generator will take not action but simply return to the start of the flow chart at block 306. If at block 304, however, the control signal generator determines that the slack voltage 30 is below the first reference voltage threshold, this would indicate that an insufficient amount of slack voltage is available and, hence, that the high voltage signal 74 is perilously close to being insufficient to allow the output state 16 to supply an electrical stimulation of proper amplitude. Thus, the control signal generator 36 at block 308 will take action to increase the high voltage signal 74 of the high voltage power supply 14 by modifying the control signals 38. A complication exists, however, if the control signal generator 36 determines, at block 302, that the slack voltage 30 is above the second reference voltage threshold. If the biological tissue stimulator is performing pulse width modulation, then excess slack voltage may occur because the particular electrical stimulation pulse being supplied may not be the maximum width pulse. If this is the case, it would not be desirable to decrease the high voltage signal 74 since the next electrical stimulation pulse may be at the maximum width and then insufficient high voltage signal would be available. Thus, the control signal generator at block 310 determines whether pulse width modulation is in operation. If pulse width modulation is not in operation, then the control signal generator at block 312 will operate to decrease the high voltage signal 74 by modifying the control signals 38 delivered to the high voltage power supply 14. Should, however, pulse width modulation be in operation, then the program must determine whether the pulse width of the electrical stimulation pulse for which the slack voltage 30 has been measured was at its maximum width. If not, the control signal generator must not modify the high voltage signal level and, hence, drop to block 306 and return to start. If, however, at block 14 the control signal generator determines that the electrical stimulation pulse for which the slack voltage 30 was measured was at its maximum width, then the control signal generator can conclude that the high voltage signal is excessive and can be decreased at block 312.

Note that the situation occurring in block 304 in which the slack voltage 30 is below the first reference voltage threshold could occur by a patient increasing the amplitude control in the output stage 16 or a changing impedance level in the biological load. In order to ensure tight tracking of the amplitude control, even at low stimulation pulse rates, it is advisable, but not required, at block 308 to increase the high voltage signal 74 to its maximum output value whenever block 308 is reached. Subsequent passes through the flow chart would, of course, reduce then excessive amounts of high voltage signal 74 should they be present. Alternatively, a control signal generator 36 could stepwise increase the high voltage signal 74 upon the occurrence of block 308 which would in time increase the high voltage signal 74 to a sufficient level to enable the output stage 16 to deliver an electrical stimulation pulse of the proper current amplitude. However, in this situation, some amount of therapeutic benefit from the desired electrical stimulation program could be lost.

Thus, there has been shown and described a novel biological tissue stimulator with adjustable high voltage power supply dependent upon load impedance. It is to be recognized and understood, however, that various changes, modifications and substitution in the form and of the details of the present invention may be made by those skilled in the art without departing from the scope of the invention as defined in the following claims.

What is claimed is:

1. A biological tissue stimulator adapted to supply an electrical stimulation signal to a biological load, comprising:
    a battery;
    a high voltage power supply operatively coupled to said battery and producing a high voltage signal;
    output means receiving said high voltage signal for supplying said electrical stimulation signal of a predetermined current amplitude;
    electrode means receiving said electrical stimulation signal and adapted to be coupled to biological tissue for delivering said electrical stimulation signal so that said electrical stimulation signal may be applied to said biological tissue; and
    adjustment means responsive to said output means and to said high voltage power supply for comparing the amplitude of said high voltage signal to the amplitude of the voltage drop across said electrode means during the application of said electrical stimulation signal to said biological tissue and adjusting the amplitude of said high voltage signal dependent upon the result of said comparing.

2. A biological tissue stimulator as in claim 1 wherein said adjustment means adjusts the amplitude of said high voltage signal to minimize the difference in amplitude between said high voltage signal and said voltage drop across said electrode means, whereby the efficiency of said biological stimulator is maximized.

3. A biological tissue stimulator as in claim 2 wherein said high voltage power supply is a switching-type power supply and with the amplitude of said high voltage signal being dependent upon control signals and wherein said adjustment means generates said control signals for said high voltage power supply.

4. A biological tissue stimulator adapted to supply an electrical stimulation signal to a biological load, comprising:
    a battery;
    a high voltage power supply operatively coupled to said battery and producing a high voltage signal whose amplitude is responsive to switching signals;
    output means receiving said high voltage signal for supplying said electrical stimulation signal of a predetermined current amplitude;
    electrode means receiving said electrical stimulation signal and adapted to be coupled to biological tissue for delivering said electrical stimulation signal so that said electrical stimulation signal may be applied to said biological tissue; and
    adjustment means responsive to said output means and to said high voltage power supply for comparing the amplitude of said high voltage signal to the amplitude of the voltage drop across said electrical means and adjusting the amplitude of said high voltage signal dependent upon the result of said comparing to minimize the difference in amplitude between said high voltage signal and said voltage drop across said electrode means;
    wherein said adjustment means comprises:
    voltage gating means coupled to said output means for gating a slack voltage representing the voltage from said high voltage signal not dissipated across said electrode means;
    a predetermined reference voltage;
    comparison means responsive to said slack voltage and said predetermined reference voltage for comparing said slack voltage to said predetermined reference voltage for producing a comparison output indicative of the result of said comparing of said comparison means relative to a predetermined threshold; and
    switching means responsive to said comparison output for supplying said switching signals so that said amplitude of said high voltage signal is properly adjusted relative to said predetermined threshold;
    whereby the efficiency of said biological stimulator is maximized.

5. A biological tissue stimulator adapted to supply an electrical stimulation signal to a biological load, comprising:
    a battery;
    a high voltage power supply operatively coupled to said battery and producing a high voltage signal whose amplitude is responsive to control signals;
    output means receiving said high voltage signal for supplying said electrical stimulation signal of a predetermined current amplitude;
    electrode means receiving said electrical stimulation signal and adapted to be coupled to biological tissue for delivering said electrical stimulation signal so that said electrical stimulation signal may be applied to said biological tissue; and
    adjustment means responsive to said output means and to said high voltage power supply for comparing the amplitude of said high voltage signal to the amplitude of the voltage drop across said electrode means and adjusting the amplitude of said high voltage signal dependent upon the result of said comparing to minimize the difference in amplitude between said high voltage signal and said voltage drop across said electrode means;
    wherein said adjustment means comprises:
    voltage gating means coupled to said output means for gating a slack voltage representing the voltage from said high voltage signal not dissipated across said biological load;
    a first predetermined reference voltage;
    a second predetermined reference voltage;
    the value of said second predetermined reference voltage being greater than the value of said first predetermined reference voltage;
    comparison means responsive to said slack voltage, to said first predetermined reference voltage and to said second predetermined reference voltage for comparing said slack voltage to said first predetermined reference voltage and producing a first comparison output indicative of such comparison, and for comparing said slack voltage to said second predetermined reference voltage and producing a second comparison output indicative of such comparison; and
    switching means coupled to said high voltage power supply and receiving said first comparison output and said first comparison output from said comparison means for supplying said control signals lowering said high voltage signal when said second comparison signal indicates said slack voltage exceeds said second predetermined reference voltage, raising said high voltage signal when said first comparison signal indicates that said slack voltage does not exceed said first predetermined reference voltage;

whereby the efficiency of said biological stimulator is maximized.

6. A biological tissue stimulator as in claim 5 wherein said switching means supplies said control signals to said high voltage power supply maintaining said high voltage signal at a level at which the value of said slack voltage is kept between said first predetermined reference voltage and said second predetermined reference voltage.

7. A biological tissue stimulator as in claim 6 wherein said gating means supplies said control signals making said high voltage signal raise to its maximum allowable value when said first comparison output indicates that the value of said slack voltage is below said first predetermined reference voltage.

8. A biological tissue stimulator adapted to supply an electrical stimulation signal to a biological load, comprising:
- a battery;
- a high voltage power supply operatively coupled to said battery and producing a high voltage signal;
- output means responsive to said high voltage signal for supplying said electrical stimulation signal of a predetermined current amplitude;
- electrode means receiving said electrical stimulation pulse and adapted to be coupled to biological tissue for delivering said electrical stimulation signal so that said electrical stimulation signal may be applied to said biological tissue; and
- adjustment means coupled to said output means and to said high voltage power supply for determining the impedance across said electrode means during the application of said electrical stimulation signal to said biological tissue and adjusting the amplitude of said high voltage and still have sufficient voltage amplitude to allow said output means to produce said electrical stimulation signal of said predetermined current amplitude;
- whereby the efficiency of said biological tissue stimulator is maximized.

9. A biological tissue stimulator as in claim 8 wherein said high voltage power supply is a switching-type power supply and with the amplitude of said high voltage signal being dependent upon control signals and wherein said adjustment means generates said control signals for said high voltage power supply.

10. A biological tissue stimulator adapted to supply an electrical stimulation signal to a biological load, comprising:
- a battery;
- a high voltage power supply operatively coupled to said battery and producing a high voltage signal;
- output means receiving said high voltage signal for supplying said electrical stimulation signal of a predetermined current amplitude;
- electrode means receiving said electrical stimulation signal and adapted to be coupled to biological tissue for delivering said electrical stimulation signal so that said electrical stimulation signal may be applied to said biological tissue; and
- adjustment means responsive to said output means and to said high voltage power supply for comparing the amplitude of said high voltage signal to the amplitude of the voltage drop across said electrode means and adjusting the amplitude of said high voltage signal dependent upon the result of said comparing;
- wherein said adjustment means adjusts the amplitude of said high voltage signal to minimize the difference in amplitude between said high voltage signal and said voltage drop across said electrode means;
- whereby the efficiency of said biological stimulator is maximized.

11. A biological tissue stimulator adapted to supply an electrical stimulation signal to a biological load, comprising:
- a battery;
- a high voltage power supply operatively coupled to said battery and producing a high voltage signal;
- output means receiving said high voltage signal for supplying said electrical stimulation signal of a predetermined current amplitude;
- electrode means receiving said electrical stimulation signal and adapted to be coupled to biological tissue for delivering said electrical stimulation signal so that said electrical stimulation signal may be applied to said biological tissue; and
- adjustment means responsive to said output means and to said high voltage power supply for comparing the amplitude of said high voltage signal to the amplitude of the voltage drop across said electrical means and adjusting the amplitude of said high voltage signal dependent upon the result of said comparing;
- wherein said high voltage power supply is a switching-type power supply and with the amplitude of said high voltage signal being dependent upon control signals and wherein said adjustment means generates said control signals for said high voltage power supply.

* * * * *

UNITED STATES PATENT AND TRADEMARK OFFICE
CERTIFICATE OF CORRECTION

PATENT NO. : 4,917,093

DATED : April 17, 1990

INVENTOR(S) : Joel R. Dufresne and William L. Sondermann

It is certified that error appears in the above-identified patent and that said Letters Patent is hereby corrected as shown below: On the title page:

Abstract, line 1, "is disclosed" should be deleted.

Col. 1, line 66, "weight Both" should read -- weight. Both --.

Col. 4, line 42, "tissue Since" should read -- tissue. Since --.

Col. 5, line 22, "not" should read -- not --.

Col. 11, line 57, "electrical" should read -- electrode --.

Col. 14, line 41, "electrical" should read -- electrode --.

Signed and Sealed this

First Day of June, 1993

Attest:

MICHAEL K. KIRK

*Attesting Officer*        Acting Commissioner of Patents and Trademarks